US00PP18627P2

(12) United States Plant Patent
Dümmen

(10) Patent No.: US PP18,627 P2
(45) Date of Patent: Mar. 18, 2008

(54) POINSETTIA PLANT NAME 'DUEAVARED'

(50) Latin Name: *Euphorbia pulcherrima*
Varietal Denomination: Dueavared

(75) Inventor: Tobias Dümmen, Rheinberg (DE)

(73) Assignee: Dümmen Jungpflanzen, Rheinberg (DE)

( * ) Notice: Subject to any disclaimer, the term of this patent is extended or adjusted under 35 U.S.C. 154(b) by 0 days.

(21) Appl. No.: 11/591,012

(22) Filed: Nov. 1, 2006

(51) Int. Cl.
*A01H 5/00* (2006.01)

(52) U.S. Cl. ..... Plt./307

(58) Field of Classification Search ..... Plt./307
See application file for complete search history.

(56) References Cited

PUBLICATIONS

Upov rom GTITM Computer Database, GTI Jouve Retrieval Software 2007/02 Citations for 'Dueavared'.*

* cited by examiner

*Primary Examiner*—Wendy Haas
(74) *Attorney, Agent, or Firm*—C. A. Whealy

(57) ABSTRACT

A new and distinct cultivar of Poinsettia plant named 'Dueavared', characterized by its compact, upright and outwardly spreading plant habit; freely branching habit; dark green and light green variegated leaves; early flowering habit; inflorescences with red-colored flower bracts; and excellent post-production longevity.

1 Drawing Sheet

Botanical designation: *Euphorbia pulcherrima.*
Cultivar denomination: 'Dueavared'.

BACKGROUND OF THE INVENTION

The present invention relates to a new and distinct cultivar of Poinsettia plant, botanically known as *Euphorbia pulcherrima* Willd., and hereinafter referred to by the name 'Dueavared'.

The new Poinsettia a product of a planned breeding program conducted by the Inventor in Rheinberg, Germany. The objective of the breeding program is to create new Poinsettia cultivars having variegated leaves, attractive floral bract coloration and excellent post-production longevity.

The new Poinsettia is a naturally-occurring branch mutation of a proprietary selection of *Euphorbia pulcherrima* Willd. identified as code number 05-005-18, not patented. The cultivar Dueavared was discovered and selected by the Inventor from within a population of plants of the parent selection in a controlled environment in Rheinberg, Germany in December, 2004.

Asexual reproduction of the new Poinsettia by terminal vegetative cuttings in a controlled environment in Rheinberg, Germany since December, 2004, has shown that the unique features of this new Poinsettia are stable and reproduced true to type in successive generations of asexual reproduction.

SUMMARY OF THE INVENTION

The cultivar Dueavared has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Dueavared'. These characteristics in combination distinguish 'Dueavared' as a new and distinct cultivar of Poinsettia:

1. Compact, upright and outwardly spreading plant habit.
2. Freely branching habit.
3. Dark green and light green variegated leaves.
4. Early flowering habit.
5. Inflorescences with red-colored flower bracts.
6. Excellent post-production longevity.

In side-by-side comparisons conducted in Rheinberg, Germany, plants of the new Poinsettia differed from plants of the parent selection in the following characteristics:

1. Plants of the new Poinsettia had variegated leaves whereas plants of the parent selection did not have variegated leaves.
2. Plants of the new Poinsettia and the parent selection differed in flower bract shape and coloration.

Plants of the new Poinsettia can be compared to plants of the Poinsettia cultivar Fiscor, disclosed in U.S. Plant Pat. No. 9,364. In side-by-side comparisons conducted in Rheinberg, Germany, plants of the new Poinsettia differed from plants of the cultivar Fiscor in the following characteristics:

1. Plants of the new Pionsettia were more compact, but broader than plants of the cultivar Fiscor.
2. Plants of the new Poinsettia had smaller leaves than plants of the cultivar Fiscor.
3. Plants of the new Poinsettia had variegated leaves whereas plants of the cultivar Fiscor had solid green-colored leaves.

BRIEF DESCRIPTION OF THE PHOTOGRAPH

The accompanying photograph illustrates the overall appearance of the new Poinsettia. These photograph shows the colors as true as it is reasonably possible to obtain in colored reproductions of this type. Colors in the photograph may differ slightly from the color values cited in the detailed botanical description which accurately describe the colors of the new Poinsettia. The photograph comprises a side perspective view of a typical flowering plant of 'Dueavared' grown in a container.

DETAILED BOTANICAL DESCRIPTION

In the following description, color references are made to The Royal Horticultural Society Colour Chart, 1995 Edition, except where general terms of ordinary dictionary significance are used. The aforementioned photograph and following observations and measurements describe plants grown in Rheinberg, Germany during the winter in a glass-covered greenhouse and under conditions and practices which approximate those generally used in commercial Poinsettia production. During the production of the plants, day and night temperatures averaged 22° C. and light levels were about 4,500 lux. Measurements and numerical values represent averages for typical flowering plants. Single plants were grown in 13-cm containers and pinched one time. Plants were about 16 weeks old when the photographs and the detailed description were taken.

Botanical classification: *Euphorbia pulcherrima* cultivar Dueavared.

Parentage: Naturally-occurring branch mutation of a proprietary selection of *Euphorbia pulcherrima* Willd. identified as code number 05-005-18, not patented.

Propagation:

*Type.*—Terminal vegetative cuttings.

*Time to initiate roots, summer.*—About nine days at 22° C.

*Time to initiate roots, winter.*—About 13 days at 22° C.

*Time to produce a rooted young plant, summer.*—About three weeks at 22° C.

*Time to produce a rooted young plant, winter.*—About four weeks at 22° C.

*Root description.*—Fibrous, fleshy; white in color.

*Rooting habit.*—Freely branching; dense.

Plant description:

*Plant habit and form.*—Compact, upright and outwardly spreading plant habit; inverted triangle. Inflorescences positioned above the foliar plane. Moderately vigorous growth habit.

*Plant height.*—About 25 cm.

*Plant diameter or spread.*—About 36.3 cm.

*Lateral branch description.*—Quantity: Freely branching habit, about six to seven lateral branches develop after pinching. Length: About 21 cm. Diameter: About 5.2 mm. Internode length: About 1.3 cm to 1.4 cm. Strength: Strong. Texture: Smooth, glabrous. Color: 137A.

*Foliage description.*—Arrangement: Alternate, simple. Length: About 8.7 cm. Width: About 7.1 cm. Shape: Ovate. Apex: Apiculate. Base: Obtuse. Margin: Lobed; dentate. Venation pattern: Pinnate. Texture, upper and lower surfaces: Smooth, glabrous. Color: Developing foliage, upper surface: Random and irregular areas of 137A and 138A. Developing foliage, lower surface: 138A. Fully expanded foliage, upper surface: Random and irregular areas of 139A and 138A; venation, 146B. Fully expanded foliage, lower surface: 137A to 137B; venation, 146B to 146C. Peitole: Length: About 5.3 cm. Diameter: About 2.1 mm. Texture, upper and lower surfaces: Smooth, glabrous. Color, upper and lower surfaces: 187A to 187b.

Inflorescence description:

*Inflorescence type and habit.*—Inflorescence are compound corymbs of cyathia with colored flower bacts subtending the cyathia. One inflorescence per lateral branch. Flowers are not fragrant. Flowers persistent. Inflorescences positioned above the foliage.

*Natural flowering season.*—Autumn/winter; inflorescence initiation and development is induced under long nyctoperiod conditions. Early flowering, response time is about 7.5 to 8 weeks.

*Post-production longevity.*—Excellent post-production longevity; plants of the new Poinsettia maintain good substance and bract color for about two months under interior conditions.

*Inflorescence size.*—Diameter: About 25 cm. Height (depth): About 5 cm.

*Flower bracts.*—Quantity per inflorescence: About 12 to 15. Length: About 11 cm. Width: About 7.9 cm. Shape: Ovate; lobed. Apex: Apiculate. Base: Obtuse. Margin: Entire; lobed. Texture, upper and lower surfaces: Smooth, glabrous. Venation pattern: Pinnate. Color: Developing or transitional bracts, upper surface: 46A. Developing or transitional bracts, lower surface: 53B. Fully developed bracts, upper surface: 46A to 46B; color becoming closer to 46C to 46D with development. Fully developed bracts, lower surface: 46C to 46D. Venation, upper and lower surfaces: Similar to flower bract color. Bract petiole: Length: About 2.6 cm. Diameter: About 2.2 mm. Texture, upper and lower surfaces: Smooth, glabrous. Color, upper and lower surfaces: 53A.

*Cyathia.*—Quantity per corymb: About ten. Diameter of cyathia cluster: About 2.7 cm. Length: About 8.7 mm. Width: About 5.7 mm. Shape: Ovoid. Color, immature: 143B. Color, mature: 143B to 143C. Nectaries: Quantity per cyathium: About one or two. Size: About 3.3 mm. Color: 15A to 15B.

*Peduncles.*—Length: About 4.5 mm. Diameter: About 1.5 mm. Strength: Strong to moderately strong. Texture: Smooth, glabrous. Color: 143C.

*Reproductive organs.*—Stamens: Quantity per cyathium: About ten. Anther shape: Oval. Anther length: About 0.5 mm. Anther color: 187A. Amount of pollen: Scarce. Pollen color: 9A. Pistils: Quantity per cyathium: One. Pistil length: About 1 cm. Style length: About 2 mm. Style color: 144B. Stigma shape: Crested. Stigma color: 59A to 59B. Ovary color: 144A. Seed/fruit: Seed and fruit production has not been observed.

Disease/pest resistance: Plants of the new Poinsettia have not been shown to be resistant to pathogens and pests common to Poinsettias.

Temperature tolerance: Plants of the new Poinsettia have been observed to tolerate temperatures ranging from about 12° C. to about 40° C.

It is claimed:

1. A new and distinct Poinsettia plant named 'Dueavared' as illustrated and described.

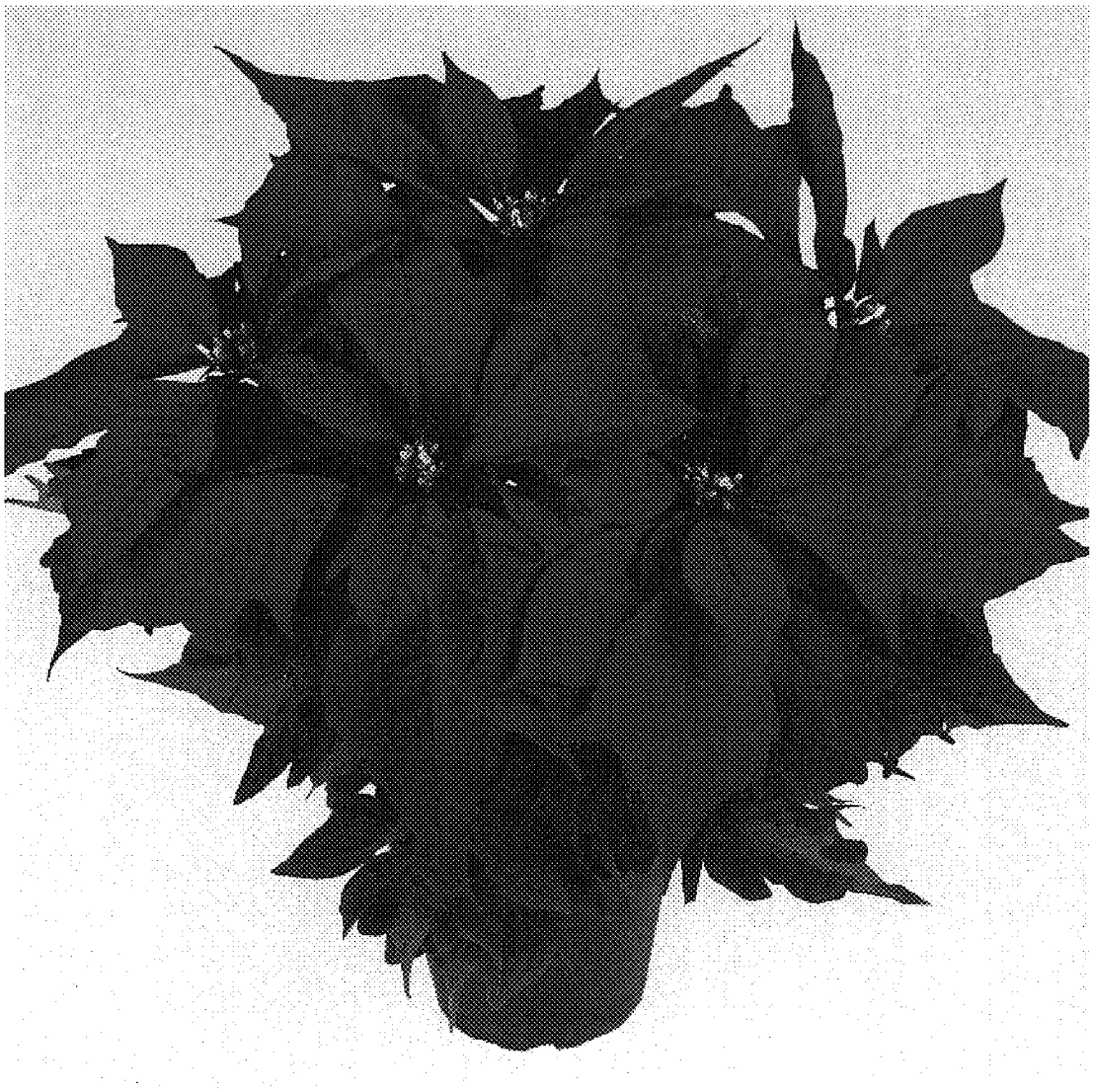

* * * * *